(12) United States Patent
Leulier et al.

(10) Patent No.: US 11,497,779 B2
(45) Date of Patent: Nov. 15, 2022

(54) GROWTH-STIMULATING LACTOBACILLUS STRAINS

(71) Applicants: Ecole Normale Superieure de Lyon, Lyons (FR); Centre National de la Recherche Scientifique (CNRS), Paris (FR); Universite Claude Bernard Lyon 1, Villeurbanne (FR)

(72) Inventors: François Leulier, Solaize (FR); Maria Elena Martino, Lyons (FR)

(73) Assignees: ECOLE NORMALE SUPERIEURE DE LYON, Lyons (FR); CENTRE NATIONAL DE LA RECHERCHE SCIENTIFIQUE (CNRS), Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 16/639,277

(22) PCT Filed: Aug. 17, 2018

(86) PCT No.: PCT/FR2018/052070
§ 371 (c)(1),
(2) Date: Feb. 14, 2020

(87) PCT Pub. No.: WO2019/034826
PCT Pub. Date: Feb. 21, 2019

(65) Prior Publication Data
US 2020/0246400 A1  Aug. 6, 2020

(30) Foreign Application Priority Data

Aug. 17, 2017 (FR) ...................... 1757717

(51) Int. Cl.
*A61K 35/747* (2015.01)
*C12N 1/20* (2006.01)
*A23L 33/135* (2016.01)
*A61K 35/00* (2006.01)

(52) U.S. Cl.
CPC .......... *A61K 35/747* (2013.01); *A23L 33/135* (2016.08); *C12N 1/205* (2021.05); *A61K 2035/115* (2013.01)

(58) Field of Classification Search
CPC .................. A61K 38/00; A61K 38/164; A61K 2035/115; A61K 35/747; A61P 29/00; C07K 14/195; C12Q 1/04; G01N 2333/195; G01N 2550/00; A23L 33/135; C12N 1/20; C12N 1/205; C12R 1/25; C12R 2001/25
See application file for complete search history.

(56) References Cited

U.S. PATENT DOCUMENTS

2014/0023693 A1* 1/2014 Guenzburg ........... A23L 29/262
424/439
2014/0234279 A1* 8/2014 Millan ...................... A61P 1/04
424/93.41

FOREIGN PATENT DOCUMENTS

WO    2010117255 A1    10/2010
WO    2015173386 A1    11/2015

OTHER PUBLICATIONS

Suo et al., "Effects of lactobacillus plantarum ZJ316 on pig growth and pork quality", BMC Veterinary Research, vol. 8, pp. 1-12 (Year: 2012).*
Aleksandrzak-Plekarczyk et al., Genome Sequence of the Probiotic Strain Lactobacillus rhamnosus (Formerly Lactobacillus casei) LOCK900, 1(4) Genome Annoucements e00640-13 1-2 (Jul./Aug. 2013).
Kankainen et al., "Comparative genomic analysis of Lactobacillus rhamnosus GG reveals pili containing a human-mucus binding protein," 106(40) PNAS 17193-17198 (Oct. 2009).
Kim et al. "Draft Genome Sequence of Lactobacillus brevis Strain EW, a *Drosophila* Gut Pathobiont," 1(6) Genome Announcements e00938-13 1 (Nov./Dec. 2013).
Koryszewska-Baginska et al., "Complete Genome Sequence of the Probiotic Strain Lactobacillus casei (Formerly Lactobacillus paracasei) LOCK919" 1(5) Genome Announcements e00758-13 1-2 (Sep./Oct. 2013).
Koryszewska-Baginska et al., "Genome Sequence of the Probiotic Strain Lactobacillus rhamnosus (Formerly Lactobacillus casei) LOCK908," 2(1) Genome Announcements e00120-14 1-2 (Jan./Feb. 2014).
Storelli et al., "Lactobacillus plantarum Promotes *Drosophila* Systemic Growth by Modulating Hormonal Signals through TOR-Dependent Nutient Sensing," 14 Cell Metabolism 403-414 (Sep. 2011).
Wang et al., "Lactobacillus plantarum ZLP001: In vitro Assessment of Antioxidant Capacity and Effect on Growth Performance and Antioxidant Status in Wearing Piglets," 25(8) Asian-Aust. J. Anim. Sci. 1153-1158 (Aug. 2012).
Yuki et al., "Survival of a probiotic, Lactobacillus casei strain Shirota, in the gastrointestinal tract: Selective isolation from faeces and identification using monoclonal antibodies". International Journal of Food Microbiology, 48, pp. 51-57 (1999).

* cited by examiner

*Primary Examiner* — Michelle F. Paguio Frising
(74) *Attorney, Agent, or Firm* — Panitch Schwarze Belisario & Nadel LLP; Erin M. Dunston

(57) ABSTRACT

The present invention concerns novel *Lactobacillus plantarum* strains capable of promoting the growth of a subject, and more particularly the juvenile or prenatal growth of farm animals, and their uses as probiotics.

21 Claims, 1 Drawing Sheet

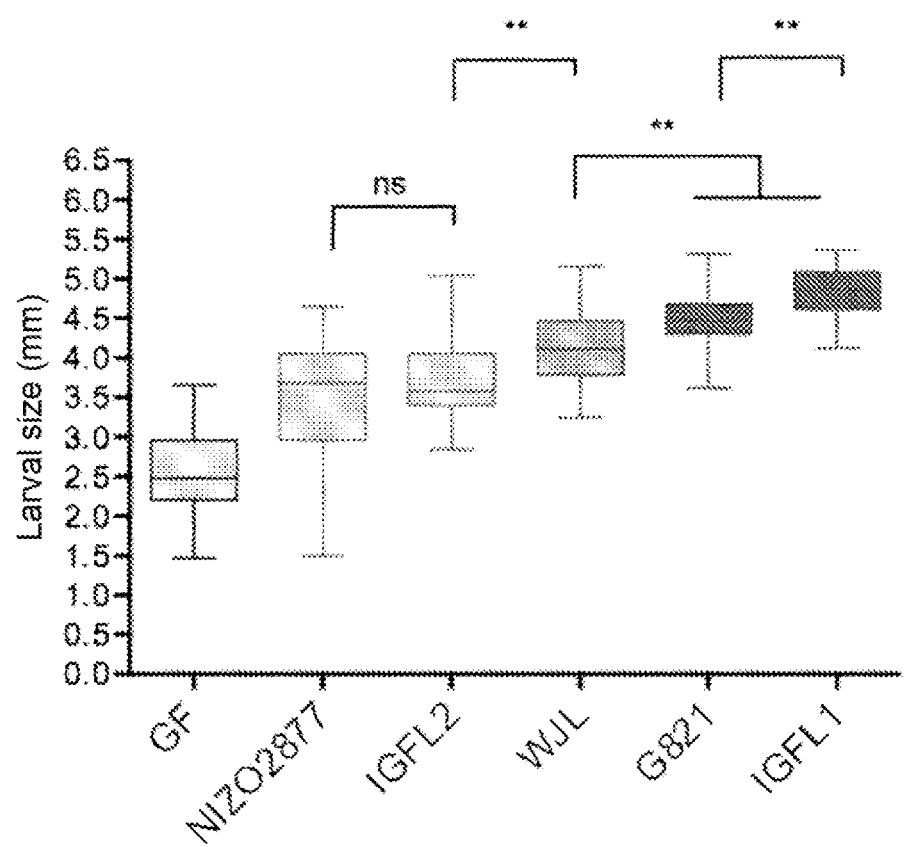

GROWTH-STIMULATING LACTOBACILLUS STRAINS

CROSS-REFERENCE TO RELATED APPLICATIONS

This application is a U.S. National Stage Application pursuant to 35 U.S.C. § 371 of International Patent Application PCT/FR2018/052070, filed on Aug. 17, 2018, and published as WO 2019/034826 on Feb. 21, 2019, which claims priority to French Patent Application 1757717, filed on Aug. 17, 2017, all of which are incorporated herein by reference in their entireties for all purposes.

The present invention concerns novel bacterial strains capable of promoting the growth of a subject, and more particularly the juvenile growth of farm animals, and their uses as probiotics. It also concerns food or pharmaceutical compositions comprising said strains, as well as their uses, in particular for enhancing the growth performance of farm animals.

TECHNOLOGICAL BACKGROUND OF THE INVENTION

Defined in 2001 by the World Health Organization (WHO) and the Food and Agriculture Organization of the United Nations (FAO), probiotics are "living microorganisms which, when ingested in sufficient quantities, exert positive health effects beyond traditional nutritional effects".

Probiotics have been marketed and used in feed for farm animals since the 1960s and have been the subject of growing interest, particularly due to the gradual reduction in the use of antibiotics as growth promoters and their ban in Europe in 2006.

Many microbial species have been used as probiotic agents. These microorganisms essentially belong to the bacteria of the genera *Bacillus, Bifidobacterium, Enterococcus, Lactobacillus, Streptococcus* and *Pediococcus*, and to the yeasts of the genus *Saccharomyces* or *Kluyveromyces*. Some of these microorganisms are usually part of the intestinal microbial community (or intestinal microbiota) while others are not usual hosts. Described as "an additional organ", this microbiota plays a key role in providing benefits to the host by performing many biological functions, such as aiding efficient digestion, substrate metabolism, pathogen control, and immune responses development and homeostasis. The use of probiotic strains therefore makes it possible to influence the composition as well as the activity of this microbiota in order to reinforce its beneficial action.

Depending on the probiotics used, their effects result either from a direct nutritional effect or from an effect linked to the strengthening of the host's natural defences. They may thus concern different aspects such as animal performance measured by zootechnical parameters or animal welfare.

In order to meet the ever-increasing demand for animal production, the search for probiotics that demonstrate a significant capacity to influence zootechnical parameters and that are capable of effectively replacing antibiotics as growth promoters is more topical than ever.

SUMMARY OF THE INVENTION

The inventors have identified novel bacterial strains capable of stimulating animal growth in a particularly effective way.

Thus, according to a first aspect, the present invention concerns a strain of *Lactobacillus plantarum* selected from the group consisting of the *Lactobacillus plantarum* strain IGFL1 deposited on 19 Jul. 2017 at the CNCM (Collection Nationale de Cultures de Microorganismes—Institut Pasteur) under number I-5217, and the *Lactobacillus plantarum* strain IGFL2 deposited on 19 Jul. 2017 at the CNCM (Collection Nationale de Cultures de Microorganismes—Institut Pasteur) under number I-5218.

According to a second aspect, it also concerns a composition comprising a *Lactobacillus plantarum* strain according to the invention, in particular a probiotic composition.

The composition according to the invention may be a food composition, preferably a food supplement or a food additive, or a pharmaceutical composition.

Preferably, the composition according to the invention comprises between $10^5$ and $10^{12}$ colony-forming units of a *Lactobacillus plantarum* strain according to the invention.

According to another aspect, the present invention also concerns a *Lactobacillus plantarum* strain according to the invention for use as a medicament, as well as the use of a *Lactobacillus plantarum* strain according to the invention for preparing a composition according to the invention.

According to another respect, the present invention concerns a *Lactobacillus plantarum* strain or a composition according to the invention for use in the treatment of growth retardation in a subject.

According to another aspect, the present invention concerns a *Lactobacillus plantarum* strain or a composition according to the invention for use in promoting the growth of a subject.

According to another aspect, the present invention concerns a non-therapeutic use of a *Lactobacillus plantarum* strain or a composition according to the invention for enhancing the growth performance of an animal.

The subject may be a human or an animal, preferably a farm animal.

According to certain preferred embodiments, the subject is a juvenile subject.

According to certain particular embodiments, the subject is a poultry, especially a poultry at a prenatal stage, i.e. in ovo.

The subject may in particular be subject to or have been subject to a nutritional deficiency, preferably a protein deficiency.

BRIEF DESCRIPTION OF THE DRAWINGS

FIG. 1: Quantification of the animal growth-promoting activity of *Lactobacillus plantarum* strains. The size data are shown in the form of box-and-whisker plots with minimum and maximum values, the median and the 50 percentiles around the median.

DETAILED DESCRIPTION OF THE INVENTION

During previous work, notably described in the international patent application WO 2015/173386, the inventors identified different *Lactobacillus* strains with a more or less marked effect on animal growth. The present invention is part of the continuation of this work and concerns novel bacterial strains with improved properties and capable in particular of strongly inducing growth. These novel strains, namely *Lactobacillus plantarum* IGFL1 and IGFL2, were isolated from natural variants of *L. plantarum* WJL and NIZO2877 strains, respectively.

Thus, according to a first aspect, the present invention concerns a *Lactobacillus* strain capable of stimulating in a particularly effective manner the growth, in particular skeletal growth, of a subject to which it is administered.

As used here, the term "subject" refers to a human or an animal. The subject may be a prenatal subject (embryo or foetus), a juvenile subject, i.e. a prepubescent human (from birth to puberty) or an animal weaned but not sexually mature, or an adult. Preferably, the human subject is a prepubescent human or an adult. The animal may be a pet, a breeding or a sport animal. Preferably, the animal is selected from dogs, cats, bovines, ovines, rabbits, porcines, caprines, equines, rodents, non-human primates and poultry. According to a preferred embodiment, the subject is a farm animal, preferably selected from bovines, ovines, rabbits, porcines, caprines, equines and poultry. According to a more particularly preferred embodiment, the subject is a poultry.

The strains according to the invention are more particularly indicated to promote the juvenile growth of subjects. Thus, according to certain embodiments, the subject is a subject at a prenatal stage (embryo or foetus) or a juvenile subject. Preferably, the subject is a juvenile subject.

According another particular embodiment, the subject is a poultry at a prenatal stage.

According to certain preferred embodiments, the subject presents or has been subjected to a nutritional deficiency, and in particular a protein deficiency. Indeed, the strains according to the invention have been shown to be particularly indicated to promote the growth, and in particular the juvenile growth, of such subjects. These subjects may be identified by weight, height and/or level of serum IGF-1 or of similar growth factor in the target species that are lower than those found in subjects of the same species, age and sex on a non-deficient diet.

As used here, the term "growth" refers to the weight gain and/or skeletal growth (also called linear growth in the case of animals without a skeleton, for example in *Drosophila*) of a subject. The skeletal growth of a subject can be easily assessed by measuring, over a given period of time, the size of individuals and/or the size of their bones, particularly their femurs. According to preferred embodiments, the term "growth" refers to the skeletal (or linear) growth of a subject.

The effect of a strain of microorganism on the growth of a subject can be assessed by any method known to the skilled person, and in particular by the methods described in the international patent application WO 2015/173386. In particular, the effect of a strain can be assessed by a test on the linear growth of *Drosophila melanogaster* larvae.

Briefly, in this test, *Drosophila* larvae, preferably axenic, i.e. without intestinal flora, are placed on petri dishes with a nutritional medium supplemented with a suspension of the strain to be tested. The larvae are incubated for several days, for example 7 days, before measuring their phenotypic characteristics, namely their weight and/or their height. The results obtained can then be compared with the results obtained with larvae incubated on nutritional medium in the absence of a microbial strain. Strains for which weight and/or height gain is significantly greater than that obtained in the absence of a microbial strain are considered to have an effect on growth. In particular, strains showing a significant positive effect (preferably with a p-value less than or equal to 0.01 in the non-parametric Mann-Whitney or Kruskal-Wallis statistical test) on the increase in larval size are considered to have a positive effect on skeletal growth. Alternatively, the results obtained can be compared with results obtained with larvae incubated on nutritional medium in the presence of a reference strain with a known positive effect on growth. In this case, the strains selected may be those with an effect equivalent or superior to the reference strain.

Conventional nutritional media used in the laboratory generally comprise at least a vegetable flour, typically maize flour, inactivated yeasts, typically *Saccharomyces cerevisiae*, agar and water. Alternatively, the medium may be a deficient medium, i.e. with a reduced content of inactivated yeast. This deficient medium does not allow optimal post-embryonic (i.e. juvenile) development of *Drosophila* larvae (Storelli et al., Cell Metabolism 14, 403-414, 2011) and can therefore be used to test the ability of strains to stimulate growth in conditions of nutritional deficiency.

In the international patent application WO 2015/173386, the inventors showed that *Lactobacillus plantarum* strains WJL, G821 and NIZO 2877 had a positive effect on growth, especially skeletal growth. As demonstrated in the experimental part of the present application, the inventors have now identified novel *Lactobacillus plantarum* strains, namely *Lactobacillus plantarum* IGFL1 and IGFL2, whose effect on growth, and in particular on skeletal (or linear) growth, surpasses that of the previously described strains.

The present invention therefore concerns a *Lactobacillus plantarum* strain selected from the group consisting of the *Lactobacillus plantarum* strain IGFL1 deposited on 19 Jul. 2017 at the CNCM (Collection Nationale de Cultures de Microorganismes—Institut Pasteur) under number I-5217, and the *Lactobacillus plantarum* strain IGFL2 deposited on 19 Jul. 2017 at the CNCM (Collection Nationale de Cultures de Microorganismes—Institut Pasteur) under number I-5218.

According to a preferred embodiment, the *Lactobacillus plantarum* strain is *Lactobacillus plantarum* strain IGFL1.

It is understood that the present invention also concerns any bacteria derived from a *Lactobacillus plantarum* strain according to the invention, in particular bacteria derived from a *Lactobacillus plantarum* strain according to the invention and having genetic modifications introduced naturally during cell divisions or by the use of genetic engineering tools. Bacteria from a *Lactobacillus plantarum* strain according to the invention preferably have an effect on the growth of a subject at least equivalent to that of *Lactobacillus plantarum* strain IGFL1 or IGFL2, preferably to that of *Lactobacillus plantarum* strain IGFL1. This effect on growth can be assessed by any method known to the skilled person, in particular by a test on the linear growth of *Drosophila melanogaster* larvae as detailed above or in the experimental section.

According to a second aspect, the present invention concerns a composition comprising a *Lactobacillus plantarum* strain according to the invention. It also concerns the use of a *Lactobacillus plantarum* strain according to the invention for the preparation of a composition according to the invention. It concerns more particularly the use of a *Lactobacillus plantarum* strain according to the invention as probiotic.

The composition according to the invention may comprise one or more strains according to the invention, namely *Lactobacillus plantarum* IGFL1, *Lactobacillus plantarum* IGFL2 or a mixture of *Lactobacillus plantarum* IGFL1 and *Lactobacillus plantarum* IGFL2.

It may also include one or more additional strains of microorganisms, especially microorganisms used as probiotics. By way of examples, the composition may include one or more additional strains of microorganism selected from the group consisting of *Bacillus, Bifidobacterium, Enterococcus, Streptococcus, Pediococcus, Saccharomyces,*

*Kluyveromyces*, and/or *Lactobacillus* such as *Lactobacillus delbrueckii, Lactobacillus plantarum, Lactobacillus fermentum, Lactobacillus casei, Lactobacillus paracasei, Lactobacillus rhamnosus*. In particular, the composition may include one or more additional *Lactobacillus* strains selected from the group consisting of *L. plantarum* WJL (Kim et al., Genome Announc. 21 Nov. 2013), *L. plantarum* G821 (deposited at the CNCM under number CNCM I-4979 on 11 May 2015), *L. plantarum* NIZO 2877, *L. casei* ATCC 393, *L. casei* L919 (Koryszewska-Baginska A et al., Genome Announc, Sep. 26, 2013), *L. paracasei* ATCC 25302, *L. paracasei* shirota (Yuki N et al., Int J Food Microbiol. Apr. 1, 1999; 48(1):51-7), *L. fermentum* ATCC 9338, *L. rhamnosus* L900 (Aleksandrzak-Piekarczyk T. et al., Genome Announc, 15 Aug. 2013), *L. rhamnosus* L908 (Koryszewska-Baginska A. et al., 20 Feb. 2014, Genome Announc.), *L. rhamnosus* GG (Kankainen M. et al., Proc Natl Acad Sci USA, 6 Oct. 2009).

According to a particular embodiment, the composition comprises one or more additional *Lactobacillus plantarum* strains, preferably selected from the group consisting of *L. plantarum* WJL, *L. plantarum* G821 and *L. plantarum* NIZO 2877.

The strain(s) contained in the composition may be living or inactivated. Preferably, the strain(s) contained in the composition are in living form. They may be in hydrated, lyophilized, frozen or any other form that allows them to be administered live to the subject. If the strains are in lyophilized form, they may be administered as such or after being reconstituted in a suitable vehicle, for example in water or other beverages. Similarly, when strains are in frozen form, they are preferably thawed prior to administration.

The composition according to the invention is preferably a probiotic composition. As used here, the term "probiotic composition" refers to a composition comprising one or more strains of probiotic microorganisms, i.e. one or more living strains which, when administered to the subject, preferably orally, exert at least one positive effect on the subject's health, for example stimulates growth. When several probiotic strains are used, they may have similar or different effects. For example, the composition according to the invention may comprise a strain according to the invention which has an effect on the growth of the subject and another strain of microorganism which has a stimulating effect on the immune system.

The composition according to the invention may be in any form suitable for its administration to the subject. According to certain embodiments, the composition according to the invention is in a form suitable for oral or rectal administration. According to other embodiments, the composition according to the invention is in a form suitable for prenatal administration, in particular by in ovo injection.

The composition according to the invention may in particular be in powder, solid, semi-solid or liquid form. According to the intended applications and the nature of the composition, it may thus be in the form of tablets, capsules, hard shell capsules, granules, powder, suspensions, emulsions, solutions or suppositories, for example. Preferably, the composition is in a gastro-resistant oral form allowing the bacteria contained in the composition, and more particularly the bacteria according to the invention, to pass through the stomach and be released in the intestine.

The composition according to the invention is preferably a food or pharmaceutical composition.

According to one embodiment, the composition according to the invention is a food composition. As used here, the term "food composition" includes any non-pharmaceutical composition intended for oral administration/use/consumption by a subject. The composition may be intended for use as food or feed. These compositions may be in particular food additives, food supplements, solid or liquid foodstuffs, in particular juices or dairy products such as milk drinks, yoghurts, cheeses or ice cream.

According to a preferred embodiment, the composition according to the invention is a food additive or food supplement. As used here, the term "food additive" refers to a composition that is intended to be mixed with one or more other foods before being administered to a subject. More particularly, the composition according to the invention may be a probiotic food additive, in particular a probiotic additive as authorized by European Directive 70/524/EC or Regulation 1831/2003/EC. The term "food supplement" refers to a composition that is formulated and administered separately from other foods and is intended to supplement a subject's nutritional intake.

According to a particular embodiment, the composition according to the invention is a feed, feed supplement or feed additive intended for animal feed, and more particularly for the feeding of farm animals.

According to another embodiment, the composition according to the invention is a pharmaceutical composition. It may be intended for use in human medicine or for a veterinary use. Preferably, the pharmaceutical composition according to the invention is a composition intended for oral, rectal or prenatal administration, more particularly by in ovo injection. According to certain embodiments, the pharmaceutical composition according to the invention is a composition intended for oral administration. According to certain other embodiments, the pharmaceutical composition according to the invention is a composition intended for prenatal administration, more particularly by in ovo injection.

The pharmaceutical composition according to the invention may comprise any pharmaceutically acceptable excipient and/or vehicle, in particular any excipient and/or vehicle suitable for oral administration or for in ovo injection. The pharmaceutically acceptable excipients and vehicles that may be used are well known to the skilled person (see for example Remington's Pharmaceutical Sciences, $18^{th}$ edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, $3^{rd}$ edition, A. Kibbe, Ed., Pharmaceutical Press [2000]).

The composition according to the invention preferably contains between $10^5$ to $10^{12}$, in particular $10^6$ to $10^{12}$, preferably $10^8$ to $10^{12}$ colony-forming units (CFU), preferably cells of a strain according to the invention, per gram of composition. "CFU" stands for the English technical term "colony-forming units". Gram of composition is preferably understood to mean the composition according to the invention comprising the bacteria according to the invention, and the appropriate co-ingredients, excipients or vehicles. As mentioned above, the co-ingredients may be in particular foods and/or other strains of microorganisms.

The present invention also concerns a *Lactobacillus plantarum* strain according to the invention for use as a medicament. It concerns in particular a pharmaceutical composition comprising a *Lactobacillus plantarum* strain according to the invention as active ingredient. The pharmaceutical composition may be as defined above.

The present invention also concerns:
- a *Lactobacillus plantarum* strain according to the invention or a composition according to the invention, preferably a pharmaceutical composition, for use in the treatment of growth retardation in a subject;
- the use of a *Lactobacillus plantarum* strain according to the invention or a composition according to the invention for the preparation of a medicament for the treatment of growth retardation in a subject; and
- a method of treating growth retardation in a subject comprising administering a therapeutically effective amount of a *Lactobacillus plantarum* strain according to the invention or a composition according to the invention, preferably a pharmaceutical composition, to said subject.

According to certain embodiments, the subject is a juvenile subject and the administration of the strain or composition according to the invention is preferably done orally.

According to certain other embodiments, the subject is at a prenatal stage, in particular a poultry at a prenatal stage, and the administration of the strain or composition according to the invention is done by in ovo injection.

A subject with growth retardation can be identified by lower weight, height and/or a serum IGF-1 level than those found in a subject of the same species, age and sex. This growth retardation can have different causes such as a nutritional deficiency, especially a protein deficiency. This deficiency may be related to chronic or acute undernutrition, or to pathophysiological malnutrition related to a patient's pathological condition. This pathological condition may in particular include motor impairment, anorexia, pathology of ingestion and/or assimilation, cachexia or sarcopenia.

The present invention concerns in particular:
- a *Lactobacillus plantarum* strain or a composition according to the invention for use in promoting the growth of a subject, preferably a juvenile subject, subjected or having been subjected to a nutritional deficiency, preferably a protein deficiency;
- the use of a *Lactobacillus plantarum* strain according to the invention or a composition according to the invention for the preparation of a medicament for promoting the growth of a subject, preferably a juvenile subject, subjected or having been subjected to a nutritional deficiency, preferably a protein deficiency; and
- a method for promoting the growth of a subject, preferably a juvenile subject, which is or has been subjected to a nutritional deficiency, preferably a protein deficiency, comprising administering a sufficient amount of a *Lactobacillus plantarum* strain according to the invention or a composition according to the invention, preferably a pharmaceutical composition, to said subject.

Preferably, said subject exhibits a growth retardation induced by this nutritional deficiency.

The therapeutically effective or sufficient amount of a *Lactobacillus plantarum* strain according to the invention or of a composition according to the invention is an amount to achieve the desired effect, namely a positive effect (an increase) on the growth of the subject.

The quantity and frequency of administration will depend on the type of subject, human or animal, the age and physiological condition of the subject, in particular the level of growth retardation and/or the level of nutritional deficiency.

The *Lactobacillus plantarum* strain or the composition according to the invention may be administered in one or more times, i.e. in the form of a single dose or multiple doses. In particular, the strain or composition according to the invention may be administered in the form of several doses staggered over the growth period of the subject, preferably until puberty or sexual maturity.

Preferably, the strain or composition according to the invention is administered to the subject at a frequency of between one dose per day and one dose per month. Typically, the frequency of administration is between one dose per day and one dose per week, in particular one dose every 2, 3, 4, 5, 6 or 7 days. Alternatively, the frequency of administration may be between several doses per day, for example 2, 3, 4 or 5 doses per day, and one dose per week.

A dose may represent several grams to several tens of grams of composition according to the invention. Typically, one dose represents between 1 and 100 g of composition according to the invention, preferably between 1 and 50 g of composition according to the invention, and more particularly preferred between 1 and 10 g of composition according to the invention. Alternatively, a dose may represent between $10^5$ and $10^{13}$ CFU, preferably between $10^6$ and $10^{12}$ CFU, of *Lactobacillus plantarum* according to the invention.

According to the subject's age or physiological condition, daily doses may be divided to facilitate administration, for example with one administration in the morning and another in the evening.

According to another aspect, the present invention concerns the non-therapeutic use of a strain or a composition according to the invention to increase the growth performance of an animal. It also concerns a method for enhancing the growth performance of an animal comprising administering a sufficient amount of a strain or a composition according to the invention to obtain a positive effect on the growth of the animal.

This positive effect may result in particular in a weight gain and/or an increase in the skeletal (or linear) growth of the animal greater than the weight gain or skeletal (or linear) growth of said animal not treated with the strain or composition according to the invention.

Preferably, the animal is a sport or breeding animal, and more particularly preferred a farm animal.

According to certain embodiments, the animal is a juvenile subject and the administration of the strain or composition according to the invention is preferably done orally. The strain or composition according to the invention is preferably administered to the animal at the same time as its normal feed ration. In particular, the composition according to the invention may be a feed additive added to the animal feed or a veterinary feed supplement.

According to certain other embodiments, the subject is at a prenatal stage, in particular a poultry at a prenatal stage, and the administration of the strain or composition according to the invention is done by in ovo injection.

All references cited in this description are incorporated by reference in the present application. Other features and advantages of the invention will become clearer when reading the following examples, which are given by way of non-limiting illustration.

EXAMPLES

Materials and Methods

D-1: adult axenic fruit flies (*D. melanogaster* strain yw) were placed in egg-laying cages with a bottom (Petri dish type) on which a conventional nutritional medium is placed (for 1 litre of medium, 7.14 g agar, 80 g maize flour and 50 g inactivated yeast, the medium is cooked in boiling water for 10 min, then cooled); egg-laying is ensured by keeping the adult population in the cage overnight at 25° C.

D0: 6 pieces of the nutritional medium were cut in order to collect 6 times 40 embryos. Each of these pieces was placed on a deficient nutritional medium contained in a Petri dish (medium comprising 6 g inactivated yeast per litre instead of 50 g per litre in the conventional medium). Three plates were inoculated with a suspension of $10^8$ CFU (colony-forming units) of the test bacteria in 1×PBS. Three other dishes (controls) were "inoculated" with sterile 1×PBS. These dishes were incubated for 7 days at 25° C.

D7: The larvae that developed were recovered from each dish (as the experiment is exploitable from 20 larvae per dish, the groups used below therefore comprise more than 60 individuals). The larvae were subjected to heat shock treatment in order to sacrifice them (5 seconds on a plate heated to 100° C.), before measuring the size of the larvae (linear measurement from the anterior to the posterior end).

This protocol was applied to different *Lactobacillus plantarum* strains (IGFL1, IGFL2, NIZO2877, WJL and G821) and the results are summarized in FIG. 1.

Results

The *Drosophila* test described above was performed with 5 *Lactobacillus plantarum* strains bacteria (IGFL1, IGFL2, NIZO2877, WJL and G821) including 3 strains previously described in the patent application WO 2015/173386 to have a more or less marked effect on the linear growth of *Drosophila* larvae, namely the strains NIZO2877, WJL and G821).

As shown in FIG. 1, *Lactobacillus plantarum* strains NIZO2877, WJL, G821, IGFL1 and IGFL2 all show growth-promoting activity in the in vivo *Drosophila* larval growth test. This test measures the growth-promoting effect of bacterial isolates based on the measurement of the length of *Drosophila* larvae (in mm) associated with the bacterial isolate under test relative to the size of control individuals not associated with bacteria (i.e. axenic). Strains NIZO2877 and IGFL2 show similar effects. On the other hand, strain IGFL1 has a statistically greater quantitative effect than all strains tested and in particular greater than strain G821 ($p<0.0067$, Kruskal-Wallis test with Dunn's multiple comparison correction) which had already been shown to have a particularly strong effect on growth (see patent application WO 2015/173386).

The invention claimed is:

1. A capsule or a tablet comprising a composition, wherein the composition consists essentially of (1) *Lactobacillus plantarum* strain IGFL1 deposited on 19 Jul. 2017 at the CNCM (Collection Nationale de Cultures de Microorganismes—Institut Pasteur) under accession number I-5217, and (2) at least one co-ingredient, excipient, and/or vehicle.

2. The capsule or the tablet according to claim 1, wherein the composition is a probiotic composition.

3. The capsule or the tablet according to claim 1, wherein the composition is a food supplement or a food additive.

4. The capsule or the tablet according to claim 1, wherein the composition comprises between $10^5$ and $10^{12}$ colony-forming units of *Lactobacillus plantarum* strain IGFL1.

5. The capsule or the tablet according to claim 1, wherein the composition is a pharmaceutical composition.

6. The capsule or tablet according to claim 1, wherein the capsule or the tablet is selected from a gastro-resistant oral capsule and a gastro-resistant oral tablet, and wherein the capsule or the tablet is capable of releasing the *Lactobacillus plantarum* strain in the intestine.

7. A method of treating growth retardation in a subject, the method comprising administering a therapeutically effective amount of a composition consisting essentially of (1) *Lactobacillus plantarum* strain IGFL1 deposited on 19 Jul. 2017 at the CNCM (Collection Nationale de Cultures de Microorganismes—Institut Pasteur) under accession number I-5217, and (2) at least one co-ingredient, excipient, and/or vehicle to a subject suffering from growth retardation.

8. The method according to claim 7, wherein the subject is a human.

9. The method according to claim 7, wherein the subject is a non-human animal.

10. The method according to claim 7, wherein the subject is a juvenile subject.

11. The method according to claim 7, wherein the subject is a poultry.

12. The method according to claim 7, wherein the subject is or has been subjected to a nutritional deficiency.

13. The method according to claim 7, wherein the subject is or has been subjected to a protein deficiency.

14. A method for promoting the growth of a subject, the method comprising administering a sufficient amount of a composition consisting essentially of (1) *Lactobacillus plantarum* strain IGFL1 deposited on 19 Jul. 2017 at the CNCM (Collection Nationale de Cultures de Microorganismes—Institut Pasteur) under accession number I-5217, and (2) at least one co-ingredient, excipient, and/or vehicle to the subject.

15. The method according to claim 14, wherein the subject is a human.

16. The method according to claim 14, wherein the subject is a non-human animal.

17. The method according to claim 14, wherein the subject is a juvenile subject.

18. The method according to claim 14, wherein the subject is a poultry.

19. The method according to claim 14, wherein the subject is or has been subjected to a nutritional deficiency.

20. The method according to claim 14, wherein the subject is or has been subjected to a protein deficiency.

21. A method for enhancing the growth performance of an animal, the method comprising administering a sufficient amount of a composition consisting of essentially (1) *Lactobacillus plantarum* strain IGFL1 deposited on 19 Jul. 2017 at the CNCM (Collection Nationale de Cultures de Microorganismes—Institut Pasteur) under accession number I-5217, and (2) at least one co-ingredient, excipient, and/or vehicle to the animal.

* * * * *